US008695407B2

(12) United States Patent
Stroock et al.

(10) Patent No.: US 8,695,407 B2
(45) Date of Patent: Apr. 15, 2014

(54) MICROTENSIOMETER SENSOR, PROBE AND METHOD OF USE

(75) Inventors: Abraham D. Stroock, Ithaca, NY (US); Alan N. Lakso, Geneva, NY (US); Vinay Pagay, Ithaca, NY (US); Bojan Ilic, Ithaca, NY (US); Meredith Metzler, Ithaca, NY (US)

(73) Assignee: Cornell University, Ithaca, NY (US)

( * ) Notice: Subject to any disclaimer, the term of this patent is extended or adjusted under 35 U.S.C. 154(b) by 275 days.

(21) Appl. No.: 13/264,964

(22) PCT Filed: Apr. 16, 2010

(86) PCT No.: PCT/US2010/031454
§ 371 (c)(1),
(2), (4) Date: Dec. 19, 2011

(87) PCT Pub. No.: WO2010/121176
PCT Pub. Date: Oct. 21, 2010

(65) Prior Publication Data
US 2012/0079876 A1 Apr. 5, 2012

Related U.S. Application Data

(60) Provisional application No. 61/170,223, filed on Apr. 17, 2009.

(51) Int. Cl.
*G01N 19/10* (2006.01)
*A01G 27/00* (2006.01)

(52) U.S. Cl.
USPC ............................................ 73/73; 137/78.3

(58) Field of Classification Search
USPC ............................................ 73/73; 137/78.3
See application file for complete search history.

(56) References Cited

U.S. PATENT DOCUMENTS 3,939,699 A * 2/1976 McCormick ...................... 73/73
4,922,945 A 5/1990 Browne
(Continued)

OTHER PUBLICATIONS

"A microfluidic embedded stem water potential sensor for grapes," A Grant Report to the Eastern Viticulture Consortium & NY Wine/Grape Foundation. 2009. pp. 1-5.*

(Continued)

*Primary Examiner* — Lisa Caputo
*Assistant Examiner* — Punam Roy
(74) *Attorney, Agent, or Firm* — Harris Beach PLLC

(57) ABSTRACT

A microtensiometer sensor includes a substrate layer fluidly coupled to an enclosed reservoir. A porous membrane is disposed on a surface of the substrate layer. The membrane defines a liquid side fluidly coupled to the reservoir and a vapor side fluidly coupled to a vapor interface. The porous membrane includes a plurality of through holes fluidly coupling the liquid reservoir to the vapor interface, and a nanoporous filler material disposed within the plurality of through holes. The filler material includes a plurality of open pores having a maximum diameter in the range of 0.2 to 200 nanometers. In one embodiment, the microtensiometer sensor includes a molecular membrane disposed adjacent to the vapor side of the porous membrane. In one example, the molecular membrane is formed of a highly crystalline polytetrafluoroethylene polymer having a microstructure characterized by nodes interconnected by fibrils. In one application, the microtensiometer sensor may be used in a probe to measure the average water potential within a network of plant or tree xylem. In another application, the microtensiometer sensor may be useful in real-time determination of the water potential in soil.

42 Claims, 6 Drawing Sheets

(56) References Cited

U.S. PATENT DOCUMENTS

| | | | |
|---|---|---|---|
| 6,263,726 | B1 | 7/2001 | Hubbell et al. |
| 6,308,563 | B1* | 10/2001 | Hubbell et al. ............ 73/152.51 |
| 7,392,697 | B2* | 7/2008 | Chikenji et al. ........... 73/152.55 |
| 7,495,302 | B2* | 2/2009 | Fischer et al. ................ 257/419 |
| 8,256,301 | B2* | 9/2012 | Jakobsen ........................ 73/721 |
| 2002/0112531 | A1 | 8/2002 | Hubbell et al. |
| 2004/0266050 | A1* | 12/2004 | Benzel et al. ................... 438/53 |
| 2005/0120813 | A1 | 6/2005 | Clark et al. |
| 2008/0041170 | A1 | 2/2008 | Jobin et al. |
| 2008/0163945 | A1* | 7/2008 | Nurse et al. .................. 137/833 |
| 2008/0271521 | A1* | 11/2008 | Skaling et al. ..................... 73/73 |
| 2010/0084333 | A1* | 4/2010 | Hoogerwerf et al. ......... 210/490 |
| 2010/0139410 | A1* | 6/2010 | Jakobsen ........................ 73/721 |
| 2010/0281992 | A1* | 11/2010 | Dannhauer et al. ............. 73/716 |

OTHER PUBLICATIONS

N. W. Choi, M. Cabodi, B. Held, J. P. Gleghorn, L. J. Bonassar, A.D. Stroock, "Microfluidic scaffolds for tissue engineering," Nature Materials, vol. 6. Nov. 2007, pp. 908-915.*

V. Pagay, A. Lakso, A. Stroock, "A microtensiometer for large-range measurement of water potential in plants, soils, and other materials," Power Point Slides, Cornell Technology Venture Forum, Oct. 20, 2011.*

Korean Intellectual Property Office, International Search Report and Written Opinion for PCT/US2010/031454 mailed on Dec. 30, 2010 (10 pgs).

International Preliminary Report on Patentability for PCT/US2010/031454 mailed on Oct. 27, 2011 (6 pgs).

* cited by examiner

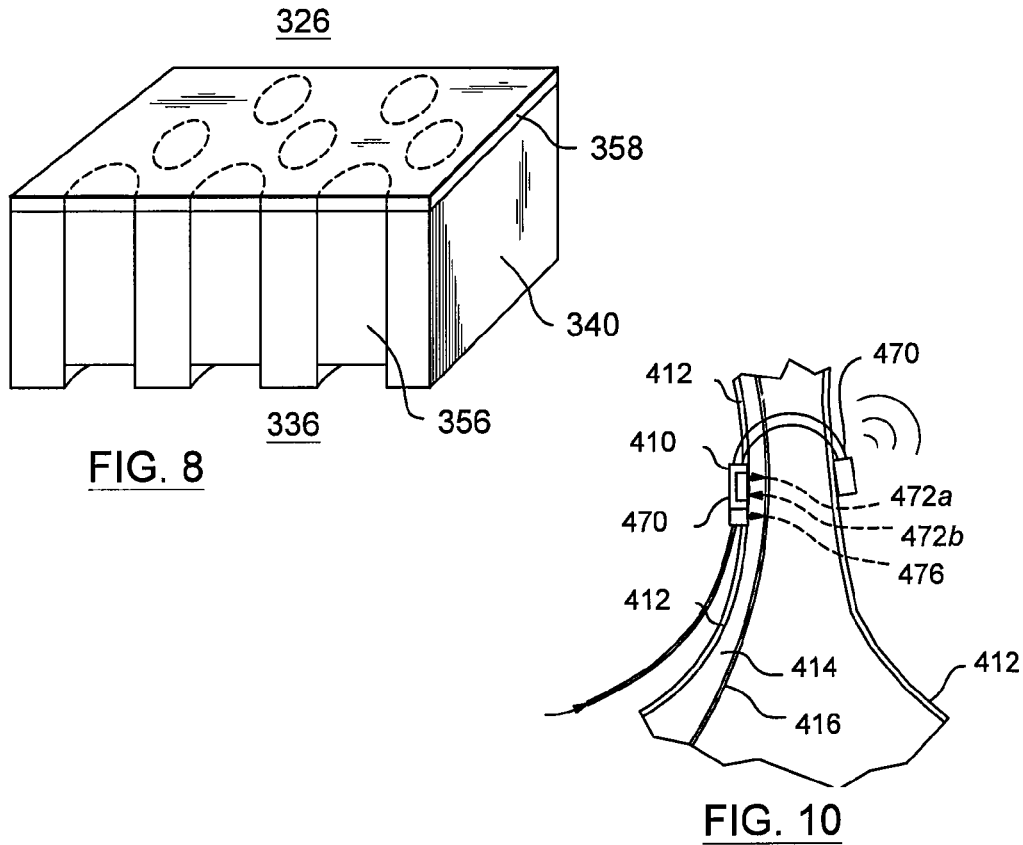
FIG. 8
FIG. 10
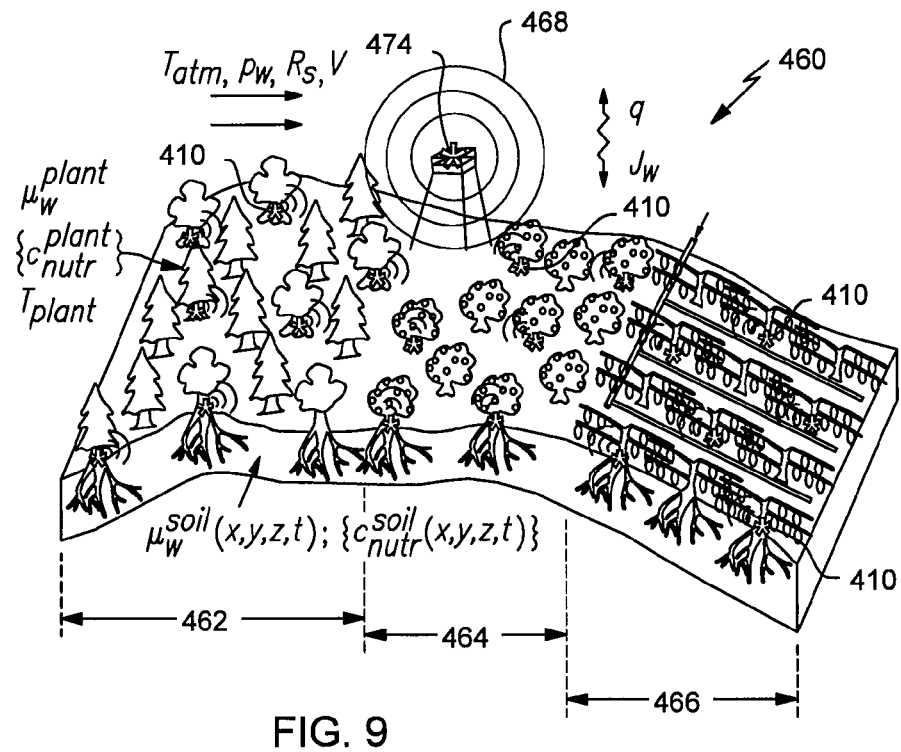
FIG. 9

MICROTENSIOMETER SENSOR, PROBE AND METHOD OF USE

CROSS REFERENCE TO RELATED APPLICATION

This application is a National Stage application under 35 U.S.C. §371 of PCT Application No. PCT/US2010/031454, filed Apr. 16, 2010, entitled "Microtensiometer," which claims priority to U.S. application Ser. No. 61/170,223, filed Apr. 17, 2009, entitled "Microfluidic Xylem Probe", which is incorporated herein by reference in its entirety.

FIELD OF THE INVENTION

This invention relates generally to microelectromechanical sensors, and more specifically, to a microfluidic microtensiometer for measuring chemical potential at negative pressures or in sub-saturated phases.

BACKGROUND OF THE INVENTION

Plants form a complex interface between the soil and the atmosphere, two spatially and temporally variable systems. In this role, plants mediate and respond to—in their growth potential, yield, and seed maturation—the mass and energy fluxes that are defined by these boundaries. Conventional agricultural and ecological assessments of the physical and chemical state of this coupled system depend on measurements of low temporal and spatial resolution in the soil and the atmosphere. Thus, the instantaneous state of the plants must be extrapolated from this indirect data, and, conversely, the role of the plants in defining their environment must be estimated via models. Furthermore, the behavior of individual plants or sub-populations within a heterogeneous environment must be deconvolved from global measurements.

Water potential ($\psi_w$) is a form of chemical potential of water ($\mu$) that is the most widely measured plant water status parameter and is a useful indicator to predict plant and fruit growth, yield, and fruit composition and quality. One advantage of using water potential to quantify plant water status is that at equilibrium, both liquid and vapor (gas) phases have identical values of water potential. "Water potential" as used herein refers to the chemical potential of sap water ($\mu_w$) relative to that of pure water ($\mu_o$) at the same temperature and atmospheric pressure, and is synonymous with "plant water status" or the "chemical potential" of the sap within the xylem. The relationship between water potential ($\psi_w$) as used by the plant scientific community and chemical potential ($\mu$) as used by the general scientific community may be expressed as:

$$\psi_W = \frac{\mu_W - \mu_o}{\overline{V_W}} \quad (1)$$

where $\overline{V_w}$ is the partial molal volume of water. For purposes of discussion herein, the term "chemical potential" will be used with the understanding that the term could also mean water potential.

Plant water relations are governed by chemical (e.g., water) potential and its gradients, not by water content. There have been many studies of the effects of water stress on plant productivity and product quality though these have not always led to predictive tools. The main problem is that in large woody plants such as trees or grapevine variations, in-water status are very dynamic, both daily and seasonally, as plant water stress responds to both soil moisture and atmospheric evaporative demand. However, the mechanisms are not yet fully understood. Part of the reason for this is that there are presently no effective tools available to easily quantify and continuously monitor plant water status. Ideal measures must be direct measurement of chemical potential, continuous to capture the dynamics, and inexpensive enough to allow spatial resolution.

Probing and determining the plant water status, or state of sap water, in xylem (the water-transporting vascular system) presents fundamental challenges. For example, during active transpiration, the xylem conduits of plants maintain an extreme physical environment. Under common physiological conditions the sap water is at large negative pressures, e.g., $P_{xylem}$<−10 atmospheres (atm.), due to extreme capillary pull generated in the leaves as evaporation occurs. The liquid is thermodynamically metastable with respect to its vapor. This metastability has been a major obstacle to the development of synthetic interfaces with xylem.

There is currently no known effective way to monitor the state of water sap continuously in the field. Soil moisture, an indirect measure, can be monitored with several methods and can be useful. However, due to the strong role of aerial evaporative demand and variable root distributions, indirect soil moisture measurement is often inadequate. Other methods have been tested in an effort to determine plant water status. For example, pressure chamber methods provide accurate measurement and allow for a direct estimate of chemical potential within the plant, but are manual, slow and do not provide continuous data. Electronic stem dendrometers provide continuous monitoring of the shrinking and swelling of the plant stem, but the relation to chemical potential is not consistent. Another method utilizes remote sensing of canopy temperature by IR thermometry or multispectral scanning, but these methods are technically complex to implement, expensive, indirect and normally only done very occasionally. Measurement of $^{13}C/^{12}C$ isotope ratios of carbon in plant tissues can be a useful integrator of water stress at over extended periods, but not for monitoring real-time. A "stem psychrometer" has been used in research to directly monitor plant water status in the stem of a plant. A stem psychrometer has a small chamber with a thermocouple junction that is cooled to reach the dewpoint of the enclosed air. The stem version has one side of the chamber open and it is sealed against the xylem of a plant to make a tight chamber. With extremely accurate measurement and control of temperature, the stem psychrometer can estimate the chemical potential at a point in the tissue. These have been used successfully by a few scientists but they are very difficult to use, are often unstable and give many artifacts. The Agricultural Electronics Corp. has manufactured the PHYTOGRAM™ sensor, comprising a metal wire embedded inside the plant tissue. The manufacturer claims to estimate the tissue hydration or water content by measuring protons in the spaces between cells. This method, however, is related to tissue water content and only indirectly to tissue chemical potential.

SUMMARY OF THE INVENTION

Disclosed is a microfluidic probe including a microtensiometer sensor coupled to a probe body. The microtensiometer sensor includes a substrate layer coupled to an enclosed reservoir, and a porous membrane disposed on a surface of the substrate layer. The membrane defines a liquid side fluidly coupled to the reservoir and a vapor side fluidly coupled to the vapor interface. The membrane includes a plurality of pores having a maximum diameter in the range of 0.2 to 200 nanometers. The microfluidic probe further includes a pressure sensor coupled to the reservoir for measuring changes to a pressure of a liquid disposed within the reservoir.

In one aspect of the invention, the porous membrane includes a plurality of through holes fluidly coupling the liquid reservoir to the vapor interface. A nanoporous filler material is disposed within the plurality of through holes. The filler material includes a plurality of open pores having a maximum diameter in the range of 1 to 100 nanometers.

In one example, the filler material is a sol-gel comprising a plurality of open pores having a maximum diameter in the range of 1 to 10 nanometers.

In another aspect of the invention, the sensor is a diaphragm-based pressure sensor comprising piezoresistive strain gauges.

In another aspect of the invention, a microtensiometer sensor is provided that includes a substrate layer fluidly coupled to an enclosed reservoir. A porous membrane is disposed on a surface of the substrate layer. The membrane defines a liquid side fluidly coupled to the reservoir and a vapor side fluidly coupled to a vapor interface. The porous membrane includes a plurality of through holes fluidly coupling the liquid reservoir to the vapor interface, and a nanoporous filler material disposed within the plurality of through holes. The filler material includes a plurality of open pores having a maximum diameter in the range of 0.2 to 200 nanometers.

In another aspect of the invention, the microtensiometer sensor further includes a molecular membrane disposed adjacent to the vapor side of the porous membrane.

In one example, the molecular membrane is a hydrophobic highly crystalline polytetrafluoroethylene polymer having a microstructure characterized by nodes interconnected by fibrils.

In another aspect of the invention, a method for measuring chemical potential in plant xylem is provided. The method includes the steps of providing a plant or tree having xylem conduits for transporting sap water, placing a microtensiometer sensor adjacent to a plurality of intact xylem conduits, equilibrating the average chemical potential of the sap water with a liquid disposed in the microtensiometer sensor, sensing a change in the chemical potential of the sap water with a pressure sensor coupled to the microtensiometer sensor, transmitting a voltage response from the pressure sensor to a transponder coupled to conductive leads of the pressure sensor, and transmitting an output from the transponder to a receiver.

In another aspect of the invention, the step of equilibrating includes exposing the sap water to a semi-permeable material that permits sap water vapor transfer and prohibits sap water liquid transfer, exposing the liquid in the reservoir to the porous membrane such that the membrane permits vapor transfer and prohibits liquid transfer, and allowing the sap water vapor to reach equilibrium with the reservoir vapor.

BRIEF DESCRIPTION OF THE DRAWINGS

The features described herein can be better understood with reference to the drawings described below. The drawings are not necessarily to scale, emphasis instead generally being placed upon illustrating the principles of the invention. In the drawings, like numerals are used to indicate like parts throughout the various views.

FIG. 8 schematically illustrates yet another embodiment of the porous membrane of the microtensiometer sensor of FIG. 3;

FIG. 9 schematically illustrates a perspective view of a water management system utilizing the microtensiometer sensor of FIG. 1 in accordance with one embodiment of the invention;

FIG. 10 schematically illustrates a perspective view of one embodiment of the water management system of FIG. 9;

DETAILED DESCRIPTION OF THE INVENTION

Microtensiometry is a required method for sensing the negative sap chemical potential in situ in the plant due to its range of measurement, accuracy, compatibility with continuous operation, and the ease with which the signal can be transduced electronically. Tensiometry allows chemical potential to be measured via the change in pressure within an enclosed volume of liquid water. Described briefly, the enclosed liquid is allowed to equilibrate with the water vapor in an external environment across a porous wick. For sub-saturated vapors (e.g., relative humidity<100%) the pressure in the enclosed liquid drops below atmospheric and reaches negative values, referred to as tension.

Monitoring water status in vines presents at least two significant drawbacks in tensiometers currently available for use in soils. One is the large form factor—existing designs are too large for direct embedding in the plant. The other drawback is insufficient range. The maximum tensions measurable with current tensiometers are approximately −1 atm., far short of the physiologically important range in vines and many other plants (e.g., down to −20 atm.). This limitation on negative pressure measurement is primarily due to the material used as the tensiometer porous wick. As the pressure within the enclosure drops, it overtakes the capillary forces holding liquid within the wick and pulls vapor into the cavity, causing the device to dry out and become inoperable. This limitation also arises from the large internal volume of liquid within conventional tensiometers (e.g., 10 milliliters). This relatively large volume is highly susceptible to cavitation or boiling of the internal liquid under tension due to homogeneous nucleation, the presence of impurities, and mechanical shocks.

In an effort to overcome these and other noted problems, the inventors have devised a microtensiometer sensor with a millimeter-scale form factor capable of measuring negative pressures down to −100 atm. In one aspect of the invention, the microtensiometer sensor is a microfluidic sensor based on microelectromechanical system (MEMS) technology for the purpose of measuring the chemical potential of water in woody plants, soils, and other systems where sub-saturated liquids or vapors exist. The sub-saturated phase is coupled to a piezoresistive pressure sensor within the microtensiometer sensor via an inorganic nanoporous membrane, the other side of which exists a discrete volume of incompressible liquid such as water. Changes in the degree of sub-saturation result in changes in hydrostatic pressure of the discrete liquid internal to the device that is sensed by the pressure sensor.

Figure 1:
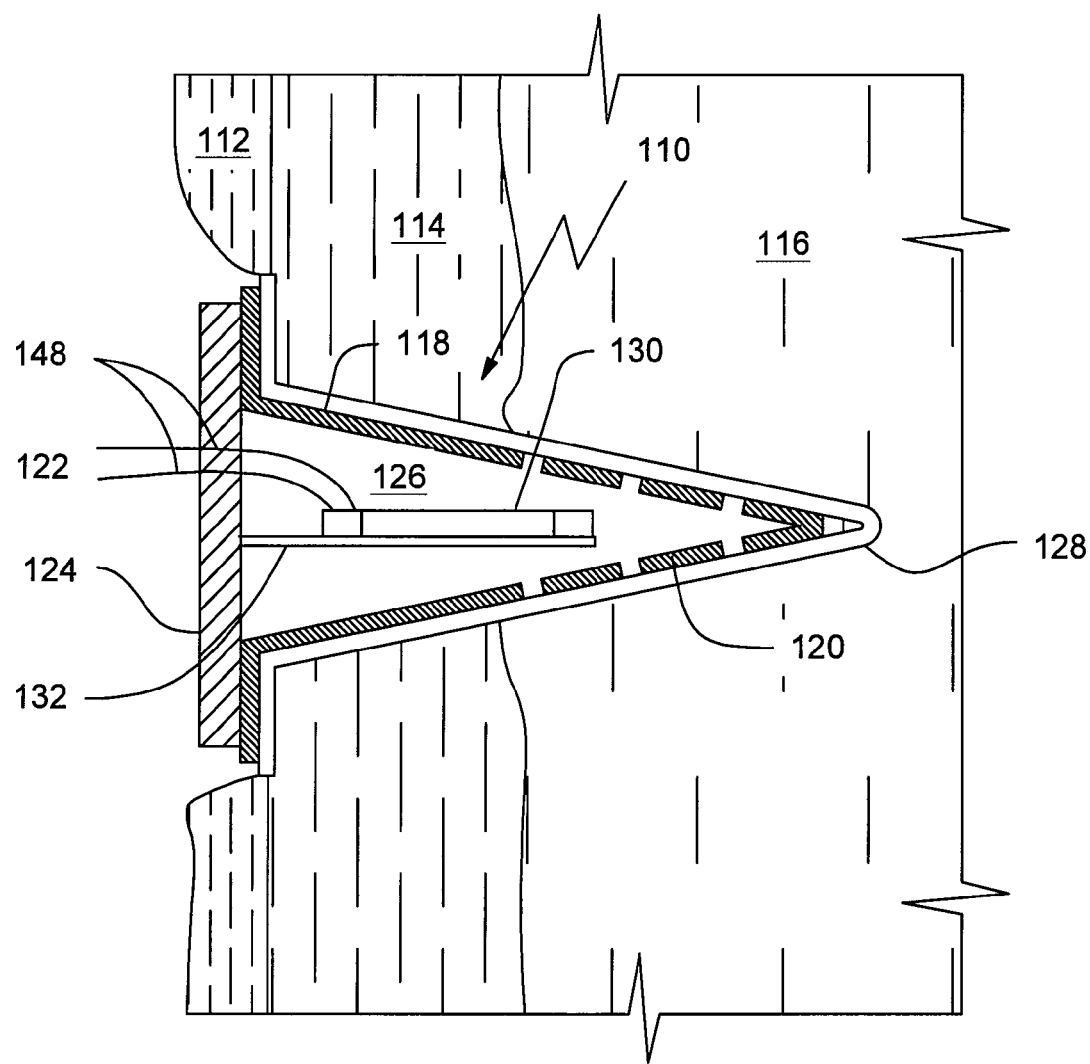
FIG. 1 schematically illustrates a cross-sectional view of a microfluidic probe in accordance with one embodiment of the invention.

Referring to FIG. 1, a microfluidic probe 110 according to one embodiment of the present invention is illustrated after insertion through a plant's bark 112 and phloem 114 into the network of plant xylem vessels 116. The microfluidic probe 110 includes a substantially solid probe body 118 with a semi-permeable tip 120 that is placed in the tissue adjacent to intact xylem conduits 116, such as xylem conduits in a grape vine or a tree, such that the chemical potential of water in the conduit 116 can equilibrate through the intervening tissue. In one example, a grapevine trunk may include between 250 and 500 xylem vessels or conduits, and the microfluidic probe 110 may measure the average chemical potential in 10 to 100 of the nearby xylem conduits 116. The semi-permeable tip 120 may be cone-shaped to ease insertion into a plant, and an opposing end 122 of the probe body 118 may include a cover 124 forming a hermetic seal with the body. The semi-permeable tip 120 functions as a fluid barrier to prevent the migration of liquid sap water across the barrier, but allow vapor transfer. In this manner, an interior portion of the probe body 118 defines a vapor interface 126 in equilibrium with the sap water within the xylem 116.

In one embodiment, the semi-permeable tip 120 may include a coating 128 thereon with specific reactivity to proteins for biocompatibility with plant xylem 116 and fusion with plant tissue. Major concerns regarding biocompatibility include fouling of external and internal surfaces of the probe 110 and rejection by the host plant. With the coating 128, the plant xylem 116 is less likely to reject the microfluidic probe 110 and may continue to grow around it. In one example, the coating 128 is a hydrogel formulation.

The microfluidic probe 110 includes a microtensiometer sensor 130 secured to the interior portion of the probe body 118. In the disclosed embodiment, the microtensiometer sensor 130 is glued to a platform 132 that is secured to the cover 124.

Figure 2:
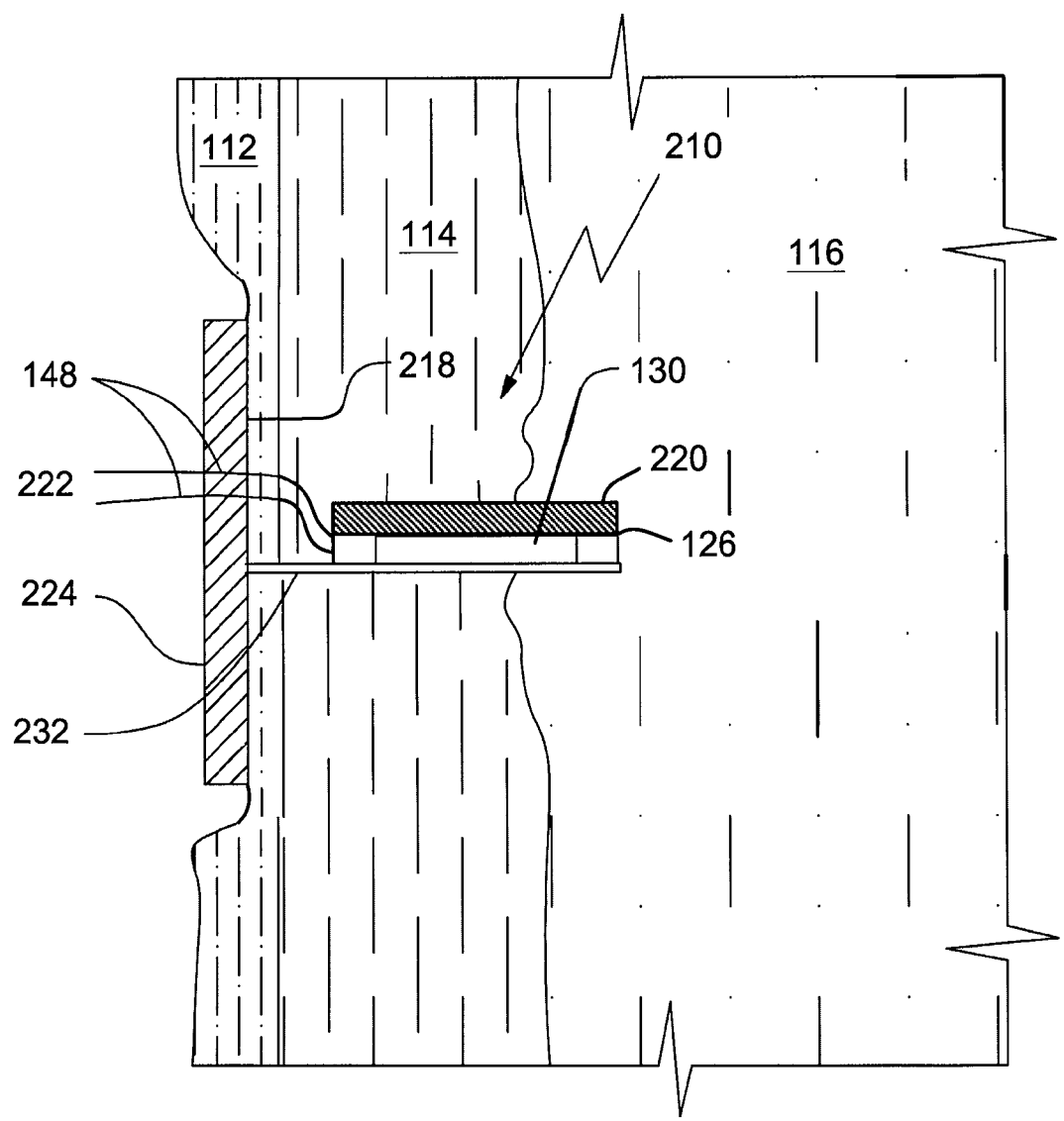
FIG. 2 schematically illustrates a cross-sectional view of a microfluidic probe in accordance with another embodiment of the invention.

Referring to FIG. 2, in another embodiment of the invention, a microfluidic probe 210 may be inserted into a slit in the plant bark 112, rather than creating a hole for a cone-shaped body. The probe body 218 includes a platform 232 and a cover 224, with the microtensiometer sensor 130 being secured to the platform 232. A semi-permeable tip 220 may comprise a hydrophobic highly crystalline polytetrafluoroethylene polymer which has a microstructure characterized by nodes interconnected by fibrils. In one example, the polytetrafluoroethylene polymer is a GORE-TEX® membrane available from W. L. Gore & Associates, Inc. The GORE-TEX® membrane may be secured to the surface of the microtensiometer sensor 130 by an adhesive backing, for example. In this embodiment, the pores in the GORE-TEX® membrane are approximately 0.02 micrometers to 10 micrometers in size, which is about 20,000 times smaller than a water droplet, but 700 times larger than a water vapor molecule. The hydrophobic GORE-TEX® membrane will therefore establish the water vapor interface 126 at the surface of the microtensiometer sensor 130. One advantage to this embodiment over the cone-shaped probe body is that the vapor interface 126 is close-coupled to the microtensiometer sensor 130, so the response time of the probe 210 may be significantly improved. Another advantage to this embodiment is that the small pore size and hydrophobicity will allow the membrane to exclude the passage of liquid water and aqueous solutions out to pressures of approximately 1 bar.

Figure 3:
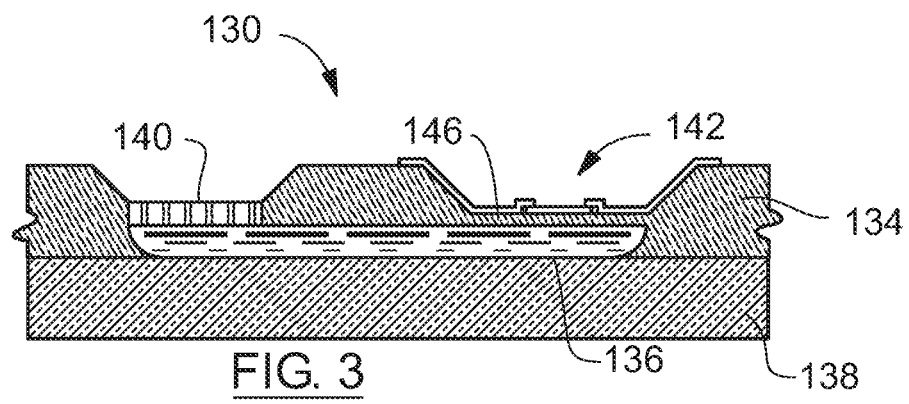
FIG. 3 schematically illustrates a cross-sectional view of the microtensiometer sensor of FIG. 1.

Turning now to FIG. 3, an exemplary microtensiometer sensor 130 includes a substrate layer 134 that serves as a backbone structure for the sensor elements. The substrate layer 134 may be fabricated from a silicon wafer, for example, due to its wide acceptance and compatibility with microfabrication techniques, such as on-substrate integration of sensing elements. Other substrate materials are contemplated without departing from the scope of the invention, such as other semiconductor materials, metals, oxides, or ceramics. However, alternate materials may not optimize the requirements for the overall design. The microtensiometer sensor 130 further includes an enclosed liquid reservoir 136. In one example, the reservoir 136 is configured to hold approximately 10 microliters of water. In one possible construction, the reservoir 136 is isotropic wet etched into a glass plate 138, and the top of the plate 138 (with the etched feature) is secured to the bottom of the substrate layer 134 by anodic bonding, thereby forming a hermetic seal to enclose the reservoir 136.

The microtensiometer sensor 130 further includes a molecularly porous membrane 140 disposed on a surface of the substrate layer 134. One side of the membrane 140 is adjacent the liquid reservoir 136, and the other side of the membrane is exposed to the vapor interface 126. Once inserted into the plant xylem 116, the vapor interface 126 of the microfluidic probe 110 reaches equilibrium with the sap water, and the liquid reservoir 136 reaches equilibrium with the vapor interface. This vapor mediated coupling to the sap water may be utilized to directly detect changes in the sap chemical potential of the xylem 116. That is, the chemical potential of the sap water may be measured via the hydrostatic pressure in the pure liquid within the tensiometer once equilibrium is achieved between the two liquids. At equilibrium, the chemical potentials of the liquid in the xylem ($\mu_w^{xylem}$) and in the tensiometer ($\mu_w^{tensio}$) are approximately equal, giving:

$$\mu_w^{xylem} = \mu_w^{tensio} = \mu_0(T) + \bar{v}(P_{tensio} - P_{atm}) \quad (2)$$

where $\bar{v}$ and $\mu_0$ are the molar volume and reference chemical potential of the pure liquid (known values). This is an approximate expression in which the liquid has been assumed to be inextensible such that $\bar{v}(P)$ equals $\bar{v}$(ambient). This approximation is good within 1% out to 100 bars of tension.

In the microtensiometer sensor 130 of the present invention, the pressure, $P_{tension}$ will be generated in the discrete volume of water coupled via the molecularly porous membrane 140 to the vapor interface 126 in equilibrium with the local sap water. The sap water in the xylem moves along gradients of chemical potential, from higher (less negative) potentials to lower potentials. The liquid water disposed in the reservoir 136 is near pure, consequently it is near zero chemical potential. The chemical potential of a plant tissue, or other material like soil for example, will be more negative because any solutes in the solution or interactions with small particles, e.g., soil, will reduce the chemical potential to negative values. Thus, there will be a gradient from the reservoir 136 in the microtensiometer sensor 130 to the xylem 116. The microtensiometer sensor 130 adjacent to the xylem 116 equilibrates via a vapor phase, and liquid will be pulled from the microtensiometer sensor to the xylem 116 tissue (or soil, for example). As some vapor moves moisture from the reservoir 136, the remaining liquid will develop tension, which is then sensed by a pressure transducer, discussed in detail below. This negative pressure reduces the chemical potential in the reservoir 136 until the chemical potential of the microtensiometer sensor 130 equals the chemical potential of the xylem 116 at equilibrium. The greater the initial difference, the more the xylem 116 will draw from the microtensiometer sensor 130 and the greater the tension (e.g., negative pressure) in the reservoir 136.

Figure 4:
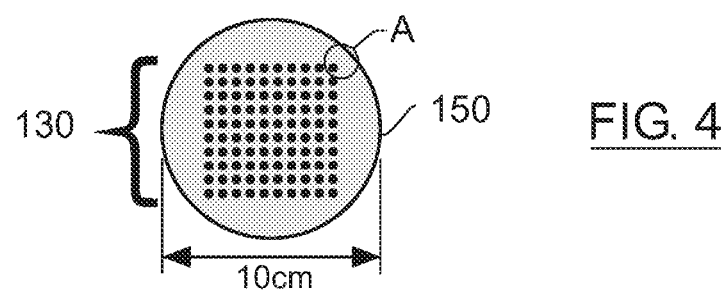
FIG. 4. schematically illustrates a top view of a silicon wafer with a plurality of the microtensiometer sensors of FIG. 3.
Figure 5:
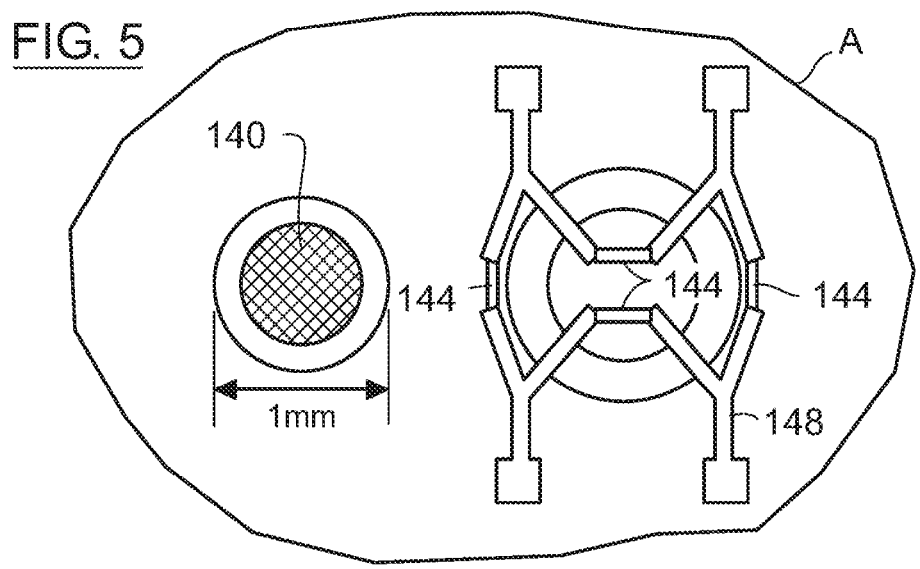
FIG. 5 schematically illustrates a top view of one of the microtensiometer sensors of FIG. 4.

The difference of hydrostatic pressure $\Delta P_{tensio} = P_{tensio} - P_{atm}$ in the liquid reservoir 136 may be transduced into a voltage with an appropriate sensor 142. Referring to FIGS. 3-5, in one embodiment the sensor 142 is a diaphragm-based pressure sensor using piezoresistive strain gauges 144 formed as thin films of poly-silicon. A diaphragm 146 may be positioned above the liquid reservoir 136, formed in the silicon substrate layer 134 using conventional fabrication techniques. Conductive leads 148 extend from the sensor 142 through the cover 124 (FIG. 1) and terminate at a data logging apparatus (not shown). Although not illustrated in FIG. 3, a support structure such as honeycomb may be necessary below the membrane 140 and the diaphragm 146 to support the thin members when large negative pressures are achieved in the reservoir 136.

Local temperature changes may affect the molar volume of the liquid in the reservoir 136, the standard chemical potential, or the response of the diaphragm 146. Accordingly, the probe 110 may further include temperature compensation circuitry. In one embodiment, the temperature compensation circuitry is integrated directly into the sensor 142. In another embodiment, the temperature compensation circuitry may comprise a stand-alone temperature probe located proximate to the microtensiometer sensor 130, such as on the platform 132. The temperature compensation circuitry may be formed by microfabrication techniques known in the art. In one example, a platinum resistance probe is constructed with four leads to allow for a "four-probe" measurement of resistance. In another example, a thin-film thermocouple may be formed by layering two materials such as gold and nickel (or gold and aluminum), each layer having thickness of approximately 300 nm.

The microtensiometer sensor 130 may comprise a microelectromechanical (MEMS) system fabricated on a silicon substrate, which are then bonded to a glass substrate to hermetically seal the internal microfluidic channel, for example. Referring to FIG. 4, a plurality of microtensiometer sensors 130 may be fabricated on a single silicon wafer or chip 150. Although early prototypes include 16 microtensiometer sensors on a wafer (each microtensiometer sensor measuring about 20×12 mm), the silicon chip 150 may include thousands of microtensiometer sensors 130.

The molecularly porous membrane 140 must have the capacity to withstand large capillary stresses in the liquid to accommodate the large negative pressures present in the sap water in the xylem 116. The relationship between the membrane maximum pore diameter $d_p^{max}$ and the maximum capillary pressure $\Delta P_{cap}^{max}$ may be expressed according to the Young-Laplace equation:

$$\Delta P_{cap}^{max} = P_{vap} - P_{liq} = \frac{4\gamma\cos\theta_r}{d_p^{max}} \quad (3)$$

where $P_{vap}$ and $P_{liq}$ are the pressures of the vapor above the pore and of the liquid in the pore, respectively, $\gamma$[N/m] is the surface tension, and $\theta_r$ is the receding contact angle in the pore (a wetting characteristic). Solving for $d_p^{max}$, $$d_p^{max} = \frac{4\gamma\cos\theta_r}{P_{vap} - P_{liq}} \quad (4)$$

Figure 6:
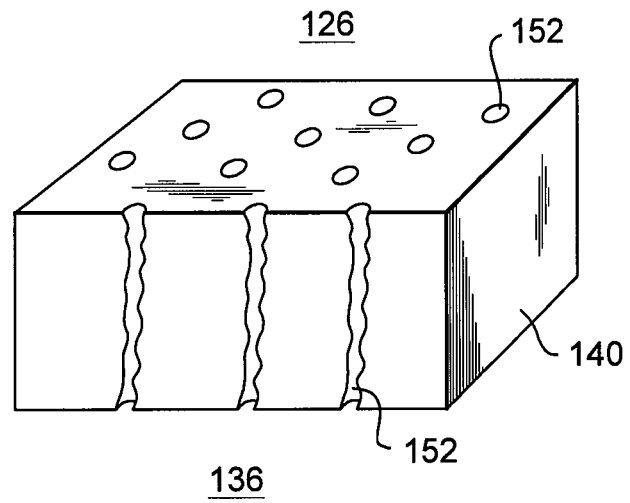
FIG. 6 schematically illustrates one embodiment of the porous membrane of the microtensiometer sensor of FIG. 3.

As can be seen with reference to Equation 3, the maximum pore diameter must be very small for the liquid to withstand the large pressure differential without vapor breakthrough. The inventors have recognized that the pore sizes in the porous membrane 140 required to hold the large negative pressures may be an order of magnitude smaller than existing structures in the art. Turning now to FIG. 6, an enlarged cross section of one possible construction of the porous membrane 140 illustrates that in one embodiment the pore structure is comprised of the interstitial voids formed in the lattice structure of the substrate layer 134. Stated another way, the pores 152 occupy the region situated in-between the atoms that corresponds to the maximum diameter sphere which can fit in the free space bounded by the neighboring atoms. The mean diameter of the interstitial voids may be calculated or determined experimentally using known techniques. The interstitial voids may be formed in the crystalline structure or the amorphous structure of silicon, for example. In the example of single crystalline silicon, the interstitial voids provide a fluid path that, although somewhat tortuous, will fluidly couple a liquid in the reservoir 136 and the vapor interface 126. In this embodiment, the pores 152 (interstitial voids) have a mean diameter in the range of 20 to 200 nanometers.

The inventors have recognized that the interstitial voids by themselves may withstand sufficient negative pressure for some applications, but to achieve very large negative pressures smaller diameter pores are required. Alternately, the maximum pore size of the naturally-occurring interstitial voids may not provide sufficient repeatability.

Figure 7:
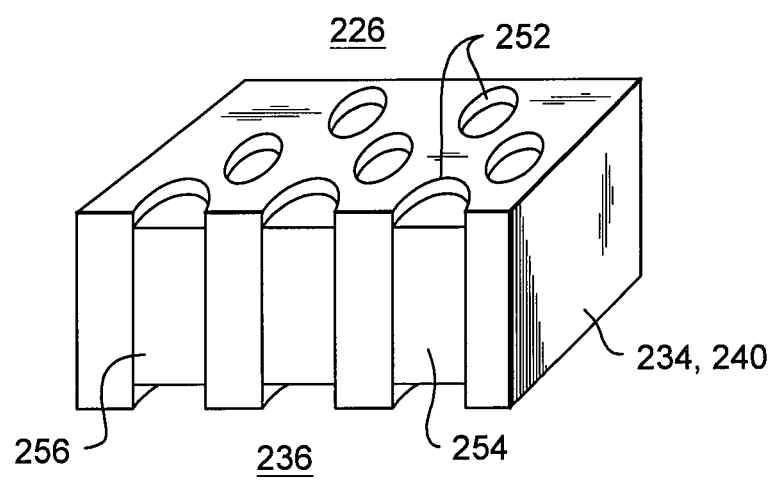
FIG. 7 schematically illustrates another embodiment of the porous membrane of the microtensiometer sensor of FIG. 3.

To that end, FIG. 7 illustrates another embodiment of a porous membrane 240. The membrane 240 includes a plurality of through holes 254 fluidly coupling a liquid reservoir 236 to a vapor interface 226. In the illustrated embodiment, the through holes 254 have a diameter in the range of 2 nanometers to 20 micrometers, and extend straight through the substrate layer 234. The through holes 254 may be formed in the silicon substrate layer 234 by electrochemically etching the silicon substrate layer through a lithographically patterned mask, chemical etching, or high temperature annealing, for example. One example fabrication method includes etching the through holes 254 from the liquid-side of the substrate layer 234, which corresponds to the bottom or underside of the layer shown in FIG. 3. As shown, the etch is performed through a portion (approximately half) of the substrate layer thickness. Then, material is removed from the opposing side of the substrate layer 234 until break-thru occurs with the through holes 254. The resulting porous membrane 240 may have a thickness in the range of 100 to 500 micrometers.

A nanoporous filler material 256 may be disposed within the plurality of through holes 254. The filler material 256 includes a plurality of molecular-scale open pores 252 fluidly coupling the liquid reservoir 236 to the vapor interface 226. The molecular-scale pores 252 may be sized to provide a pre-determined pressure differential across the porous membrane 240, in accordance with Equation 3 above. As used herein, the term "open pore" means an open passageway from the vapor-side to the liquid-side of the substrate. The open passageway may be straight-through, tortuous, or branched. In one embodiment, the filler material 256 comprises a molecular gel. As used herein, a molecular gel is a cross-linked system comprising an amorphous mixture of an interconnected phase and a solvent. The three-dimensional cross-linked network within the solvent provides a molecular-scale pathway through the structure of the gel, herein referred to as the open pores. The diameter of the pores 252 in the molecular gels range from 1 to 100 nanometers. The molecular gel may include both organic forms and inorganic forms. In one example, an organic form is a hydrogel.

In another example, an inorganic form is a sol-gel. One example of a sol-gel that is particularly well-adapted for use in the present invention is an amorphous silica sol-gel comprising a tetraethoxysilane precursor and having a pore size in the range of 1 to 2 nanometers. With reference to the equations above, this filler material 256 may provide negative pressures in the liquid reservoir 236 of less than −100 atmospheres (−10 megapascals). The sol-gel may be formed via spin-coating the precursor solutions onto the etched through holes 254. Alternately, the composite comprising porous silicon and silica sol-gel may be formed in the through holes 254 by drop-casting the pre-gel solution onto the porous matrix. The reagents will wick into the through holes 254 prior to thermal curing in ethanol.

In other examples, the filler material 256 may comprise nanoporous materials such as zeolytes, ceramics, and porous oxides such as alumina and silica. The size of the pores 252 in these examples may range from 0.2 nanometers (for zeolytes) to 200 nanometers (for porous silicon). In one example, the filler material 256 is porous silicon having a mean pore diameter of approximately 20 nanometers. The corresponding negative pressure in the liquid reservoir 236 may be less than −0.1 atmospheres (−0.01 megapascals), and in some examples, may be less than −100 atmospheres (−10 megapascals).

Turning to FIG. 8 of the drawings, yet another embodiment of a porous membrane 340 is shown wherein a molecular membrane 358 is disposed adjacent to a filler material 356 to add an extra measure of robustness. In one example, the molecular membrane 358 is a wicking hydrogel membrane disposed on the vapor-side of the porous membrane 340. The inventors have determined that the hydrogel membrane 358, being a molecular-scale mixture of polymer and water, is able to mediate the generation of negative pressures through an osmosis-like mechanism and provides excellent wicking capability. In another example, the molecular membrane 358 comprises a solution of acrylate monomer (or oligomers), a cross-linker, an initiator, and an acrylo-silane binder. The hydrogel solution may be spin cast onto the external surface of the sol-gel filled, porous silicon, then cured.

The molecular membrane 358 may be utilized to ease manufacturing and reduce costs. In one example, the porous membrane 340 may have relaxed tolerances on pore diameter, thereby making it cheaper to produce. Since the pressure differential from the vapor interface 326 to the reservoir 336 is dependent upon the largest pore diameter (Eq. 4), the pore size in the porous membrane 340 may be relaxed without adversely affecting the maximum achievable pressure differential, as long as the pore diameter in the molecular membrane 358 remains tightly controlled. In this manner, a hierarchically structured or graduated membrane may be constructed within the scope of the invention.

In another embodiment, the molecular membrane 358 comprises a non-wicking (e.g., hydrophobic) highly crystalline polytetrafluoroethylene polymer which has a microstructure characterized by nodes interconnected by fibrils. In one example, the polytetrafluoroethylene polymer is a GORE-TEX® membrane available from W. L. Gore & Associates, Inc. In this embodiment, the pores in the GORE-TEX® membrane are approximately 0.02 micrometers to 10 micrometers in size, which is about 20,000 times smaller than a water droplet, but 700 times larger than a water vapor molecule. The GORE-TEX® membrane will therefore establish a water vapor interface at the surface of the porous membrane 340.

The disclosed microfluidic probe may benefit agricultural crop producers, such as wine grape growers, because the probe allows dynamic data gathering to predict the effect of water stress on the overall vineyard or on portions thereof. In a broader sense, data gathered may also lead to proper regulation of irrigation to impose an intended water deficit to achieve the desired fruit style with higher reliability. Turning now to FIGS. 9 and 10, a water management system 460 includes a plurality of microfluidic probes 410 to provide precision ecology and agriculture. In one example, a tract of land may include a forest portion 462, an orchard portion 464, and a vineyard portion 466, each having variable soil conditions such as chemical potential and nutrient concentrations, $\mu_w^{soil}$ and $\{c_w^{soil}\}$, respectively. The portions of the tract 462, 464, 466 further include variable atmospheric conditions such as temperature, $T_{atm}$, vapor pressure, $p_w$, solar radiance, $R_s$, and wind speed V. The plurality of microfluidic probes 410 may allow for monitoring and control of water ($\mu_w^{plant}$) and nutrient ($\{c_{nut}^{plant}\}$) status directly in plants using a wireless interface 468. The probe data may allow for closure of mass and energy balances, ($J_w$[moles/(m²s)]) and (q [W/m²]), respectively.

FIG. 10 illustrates the microfluidic probe 410 with a wireless transponder 470 bound to the bark 412 of a woody plant. In one embodiment, the probes 410 make multiple insertions to the xylem 416 conduits of the plant to assess the health of the plant and provide nutrients according to a pre-determined schedule. A first insertion point includes an analytical xylem tap 472a for sensing chemical potential $\mu_w^{plant}$. A second insertion point includes an analytical xylem tap 472b for sensing nutrient concentration $\{c_{nut}^{plant}\}$. Data gathered from the water dynamics and nutrient content may be broadcast from the wireless transponder 470 to a receiver 474 at a control point where data is gathered from all the other probes 410. The interfaces may allow for the transmission and remote logging of data from sensors as well as those from conventional thermocouples and air hygrometers deployed on the plant. The data may be compared to historical or desired properties, for example, and corrective action may be undertaken to alter the chemical potential or nutrient content in any number of plants.

In one example, the current state of chemical potential is determined to be higher than desired, meaning the plant may be experiencing undue stress from lack of moisture. A feedback action may be initiated responsive to the data reading, such as actuating an irrigation system. The action may continue until current readings indicate the chemical potential is within acceptable limits In one example, the water (or nutrient) is added via a feedback-controlled supply tap 476 for direct delivery to the xylem 416.

Figure 11:
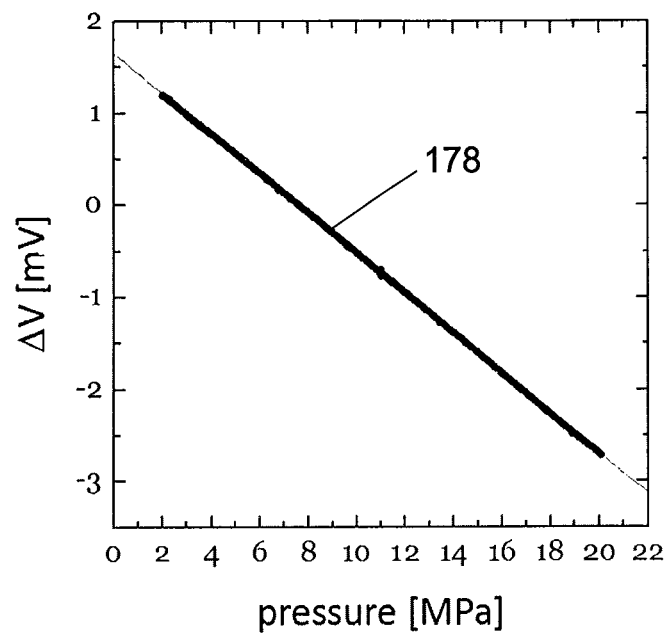
FIG. 11 graphically illustrates a response of the pressure sensor of the microtensiometer sensor of FIG. 3.
Figure 12:
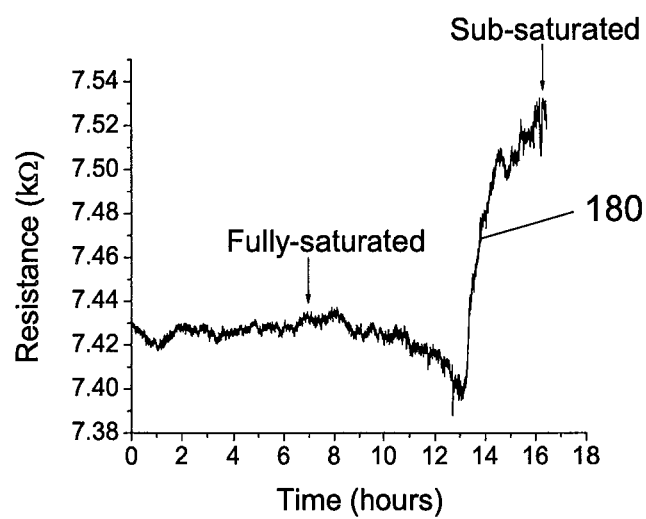
FIG. 12 graphically illustrates a response of the microtensiometer sensor of FIG. 3.

FIGS. 11 and 12 graphically illustrate test data obtained from prototypes of the microtensiometer sensor 130 disclosed herein. The microtensiometer sensor 130 was microfabricated on a silicon substrate 150, which was then bonded to a glass substrate plate 138 to hermetically seal the internal microfluidic channel 136, as described hereinabove. To fill the channel 136, water was pressurized through the nanoporous exchange membrane 140 at approximately 10 MPa (100 bars) until the internal channel and cavity 136 were filled. The microtensiometer sensor 130 was then removed from the pressure chamber and placed in a sub-saturated environment of saturated salt, which set the activity of the vapor interface 126 and, therefore, the degree of sub-saturation. Changes in sub-saturation were measured using the pressure sensor 142 as its diaphragm deflected in response to changes in internal pressure of water as it equilibrated with the sub-saturated phase.

FIG. 11 illustrates a characteristic response 178 of the piezoresistive pressure sensor 142 used in the prototype testing. The data shows a linear response to positive external hydrostatic pressure up to 200 bars (20 MPa).

FIG. 12 illustrates a response 180 of the microtensiometer sensor 130 to sub-saturated vapor at −33 bars as defined by the saturated salt. Increased resistance indicates lower internal fluid pressure and external vapor sub-saturation or water potential.

The disclosed microfluidic probe has particular potential for use in measuring the chemical potential in grapevines. Water status not only determines growth in grapevines, but there is also recent evidence that water status is a critical component of terroir, or the special characteristics that geography, climate and culture bestows upon wines from specific locations (e.g., Burgundy, France). The effect of water stress on fruit and wine quality is a high priority on national wine industry surveys, reflecting the industry's understanding of this relationship. But the invention is not so limited. The inventors contemplate the microfluidic probe may be used to measure chemical potential in virtually any type of tree, including any variety of fruit tree or forest trees. The microfluidic probe may further be adapted to measure chemical potential in annual plants and the like, but the probe body and/or coating on the semi-permeable tip may require small modifications due to the soft tissue on the plants.

An additional use of the microfluidic probe may be to measure the chemical potential in soil replacing the current large soil tensiometers to provide a much greater and more useful range of chemical potentials. In one application of the invention, real-time measurements of soil water potential can be made. Current methods assess soil water status by measuring soil water content or soil water potential. Soil water content is measured using feel and appearance, the gravimetric technique, or using instruments such as neutron probes, or time-domain or frequency-domain reflectometers. However, these techniques are prone to errors and have limitations. For example, neutron probes have a radioactive source and therefore requires a licensed professional to operate the instrument while reflectometers, although very accurate, tend to be expensive. Soil water content is better for calculating soil water budgets and water use of plants, but does not give a direct measure of plant stress. The relationship between soil water content and soil water potential is non-linear, but due to the heterogenous nature of soils, the mathematical description of the relationship varies for each type of soil and cannot be easily predicted. Additionally, as soil changes with depth and roots occur across this variation, predicting plant water potential from soil water content is exceedingly difficult. Consequently, soil water content is rarely used to estimate soil water potential. Very general empirical relationships between soil water content and plant performance are used (for example, with a given soil and plant a 50% depletion of the plant-available soil water may found from grower experience to relate to initial losses in yield). Soil water tension is measured by instruments such as porous (typically ceramic or gypsum) blocks and tensiometers. Porous blocks can be problematic in alkaline soils (they break down) and erroneous in saline soils due to high electrical conductivity of the soil solution. Current soil tensiometers have a practical operating range of only 0 to 75 centibars (0 to 0.075 megapascals), which may be adequate for coarse-textured soils but inadequate for fine-textured soils such as silt loams and clay loams. They are useful for irrigation scheduling to avoid any stress, but are not suited for measuring even moderately dry soil. They also require refilling of the water reservoir on a regular basis (depending on soil dryness).

Owing to its very small form factor, the disclosed microtensiometer sensor may have useful applications in environments other than plant xylem or soils. In one example, the microtensiometer sensor may be utilized in food preparation industries as a means for measuring the water potential in foods such as cereals.

In another example, the microtensiometer sensor may be used to determine the water potential, and thus indirectly the water content via a potential-to-content calibration, of industrial, chemical, or materials processes. One process includes making concrete. Concrete solidifies and hardens after mixing with water due to hydration, wherein the water reacts with the cement and bonds the other components together, eventually creating a strong stone-like material. The curing process of the concrete after it has been placed is important to achieving the best strength. Concrete requires a moist, controlled environment to properly cure, especially within the first three days. The concrete paste hardens over time, initially setting and becoming rigid though very weak and gaining in strength in the following weeks.

During the first few days, concrete needs to be kept under a controlled temperature and humid atmosphere. The water status of concrete is critical to the drying and curing process. The water status affects the shrinkage during drying and the final product strength. Abnormally fast drying and shrinkage due to factors such as evaporation from wind during placement may lead to increased tensile stresses at a time when it has not yet gained sufficient strength, resulting in greater shrinkage cracking. Minimizing stress prior to curing minimizes cracking.

Prior studies attempting to correlate water potential and concrete shrinkage have used a thermocouple psychrometer, which is an expensive instrument that works by a different principle than that disclosed herein. The studies found a close correlation between measured water potential and concrete shrinkage, with water potentials varying from 0 to −6 MPascals (0 to −60 bars). Other methods include a very slow drying of concrete samples for 16 hours in a microwave (AASHTO) or using a very expensive time domain reflectometry coupled to fiber optics.

Although the effects of water content on the curing of concrete are documented, the known methods of controlling the moisture content are crude, such as spraying or ponding (submerging setting concrete in water and wrapping in plastic to contain the water in the mix). These methods protect the concrete mass from ill effects of ambient conditions. Additional common curing methods include wet burlap and/or plastic sheeting covering the fresh concrete, or by spraying on a water-impermeable temporary curing membrane.

The disclosed microtensiometer sensor can potentially be used to monitor and even control the moisture content of setting concrete to obtain optimum strength and durability. The disclosed microtensiometer sensor has a large range suitable for concrete manufacturing, potentially a very low cost to produce using commercial micro-manufacturing techniques, and the accuracy of the sensor and inexpensive readout represent great improvements over any current sensor.

One advantage of the disclosed microtensiometer sensor is that the large negative water pressures (less than −10 atm.) present in plant xylem may be directly measured to aid in determining the water content and ultimately the health of the plant, vine, or tree.

Another advantage of the disclosed microfluidic xylem probe is that they are compatible with long-term deployment directly within the primary vascular system of plants (xylem) and could therefore revolutionize the management of high value crops and the refinement of ecological and climatological data and models.

Yet another advantage of the disclosed microfluidic xylem probe is that real-time data may be obtained on a continuous basis, allowing scientists to correlate soil and climate models with actual responses in the chemical potential of the plant.

A general advantage of tensiometry is the potential for high accuracy at very high relative humidity ($\Delta P_{tensio}$=1 bar at RH=99.99%). A particular advantage of the disclosed MEMS tensiometer is the potential to extend the functional range of tensiometry to −85% RH (for water). Conventional tensiometers fail for RH<~99% RH. Improvements in performance due to membrane design and small internal volume.

While the present invention has been described with reference to a number of specific embodiments, it will be understood that the true spirit and scope of the invention should be determined only with respect to claims that can be supported by the present specification. Further, while in numerous cases herein wherein systems and apparatuses and methods are described as having a certain number of elements it will be understood that such systems, apparatuses and methods can be practiced with fewer than the mentioned certain number of elements. Also, while a number of particular embodiments have been described, it will be understood that features and aspects that have been described with reference to each particular embodiment can be used with each remaining particularly described embodiment. For example, although the liquid in the reservoir has been described as pure water, other liquids are contemplated within the scope of the invention, such as alcohols or organic solvents.

We claim:

1. A microfluidic probe comprising:
a probe body; and
a microtensiometer sensor coupled to the probe body, the microtensiometer sensor comprising a substrate layer fluidly coupled to an enclosed reservoir, a porous membrane disposed on a surface of the substrate layer, the membrane defining a liquid side fluidly coupled to the reservoir and a vapor side fluidly coupled to a vapor interface, the membrane comprising a plurality of pores extending from the vapor interface to the reservoir, the pores having a maximum diameter in the range of 0.2 to 200 nanometers, the microtensiometer sensor further comprising a pressure sensor coupled to the reservoir for measuring changes to a pressure of a liquid disposed within the reservoir.

2. The microfluidic probe of claim 1, wherein the probe has a millimeter-scale form factor.

3. The microfluidic probe of claim 1, further comprising a hollow semi-permeable tip joined to the probe body, the hollow semi-permeable tip defining the vapor interface.

4. The microfluidic probe of claim 3, wherein the semi-permeable tip is cone-shaped.

5. The microfluidic probe of claim 3, wherein the semi-permeable tip is formed of a hydrophobic highly crystalline polytetrafluoroethylene polymer having a microstructure characterized by nodes interconnected by fibrils.

6. The microfluidic probe of claim 3, wherein the semi-permeable tip comprises a coating thereon with specific reactivity to proteins for biocompatibility with plant xylem.

7. The microfluidic probe of claim 6, wherein the coating is formed of a hydrogel.

8. The microfluidic probe of claim 1, further comprising a transponder coupled to the pressure sensor for transmitting pressure data to a receiver.

9. The microfluidic probe of claim 8, wherein the transponder is a wireless transponder.

10. The microfluidic probe of claim 1, wherein the plurality of pores are interstitial voids formed in the lattice structure of the substrate layer.

11. The microfluidic probe of claim 10, wherein the mean diameter of the interstitial voids are in the range of 20 to 200 nanometers.

12. The microfluidic probe of claim 1, wherein the porous membrane comprises a plurality of through holes fluidly coupling the liquid reservoir to the vapor interface and a nanoporous filler material disposed within the plurality of through holes, the filler material comprising a plurality of open pores having a maximum diameter in the range of 1 to 100 nanometers.

13. The microfluidic probe of claim 12, wherein the through holes have a diameter in the range of 1 to 10 micrometers.

14. The microfluidic probe of claim 12, wherein the filler material is formed of a molecular gel.

15. The microfluidic probe of claim 14, wherein the molecular gel is a sol-gel.

16. The microfluidic probe of claim 15, wherein the sol-gel comprises a plurality of open pores having a maximum diameter in the range of 1 to 10 nanometers.

17. The microfluidic probe of claim 14, wherein the molecular gel is a hydrogel.

18. The microfluidic probe of claim 1, wherein the sensor is a pressure sensor.

19. The microfluidic probe of claim 18, wherein the pressure sensor is a diaphragm-based pressure sensor comprising piezoresistive strain gauges.

20. The microfluidic probe of claim 19, wherein the strain gauges are formed as thin films of poly-silicon.

21. The microfluidic probe of claim 1, further comprising a cover coupled to the probe body, the pressure sensor having conductive leads for transmitting a voltage responsive to the changes in pressure of the liquid in the reservoir, the conductive leads extending from the pressure sensor through the cover.

22. A microtensiometer sensor, comprising:
a substrate layer fluidly coupled to an enclosed reservoir;
a porous membrane disposed on a surface of the substrate layer, the membrane defining a liquid side fluidly coupled to the reservoir and a vapor side fluidly coupled to a vapor interface, the porous membrane comprising a plurality of through holes fluidly coupling the liquid reservoir to the vapor interface and a nanoporous filler material disposed within the plurality of through holes, the filler material comprising a plurality of open pores having a maximum diameter in the range of 0.2 to 200 nanometers; and
a pressure sensor coupled to the reservoir for measuring changes to a pressure of a liquid disposed within the reservoir.

23. The microtensiometer sensor of claim 22, wherein the through holes have a diameter in the range of 1 to 10 micrometers.

24. The microtensiometer sensor of claim 22, wherein the filler material is formed of a molecular gel.

25. The microtensiometer sensor of claim 24, wherein the molecular gel is a sol-gel.

26. The microtensiometer sensor of claim 25, wherein the sol-gel comprises a plurality of open pores having a maximum diameter in the range of 1 to 10 nanometers.

27. The microtensiometer sensor of claim 24, wherein the molecular gel is a hydrogel.

28. The microtensiometer sensor of claim 22, wherein the pressure sensor is a diaphragm-based pressure sensor comprising piezo-resistive strain gauges.

29. The microtensiometer sensor of claim 28, wherein the strain gauges are formed as thin films of poly-silicon.

30. The microtensiometer sensor of claim 22, further comprising a molecular membrane disposed adjacent to the vapor side of the porous membrane.

31. The microtensiometer sensor of claim 30, wherein the molecular membrane is formed of a wicking hydrogel membrane.

32. The microtensiometer sensor of claim 30, wherein the molecular membrane is formed of a hydrophobic, highly crystalline polytetrafluoroethylene polymer which has a microstructure characterized by nodes interconnected by fibrils.

33. A method for measuring water potential, comprising the steps of:
    placing a microtensiometer sensor adjacent to a substance having a water potential to be measured, the microtensiometer sensor having a millimeter-scale form factor;
    forming a water vapor interface between the microtensiometer sensor and the substance;
    equilibrating the average water potential of the substance with a liquid disposed in the microtensiometer sensor;
    sensing a change in the average water potential of the substance with a pressure sensor coupled to the microtensiometer sensor;
    transmitting a voltage response from the pressure sensor to a transponder coupled to conductive leads of the pressure sensor; and
    transmitting an output from the transponder to a receiver.

34. The method of claim 33, wherein the microfluidic tensiometer comprises:
    a substrate layer having an enclosed liquid reservoir formed therein;
    a porous membrane disposed on a surface of the substrate layer, the membrane comprising a plurality of pores fluidly coupling the liquid reservoir to a vapor interface of the sap water; and
    wherein the pressure sensor is coupled to the liquid reservoir for measuring changes to pressure in the liquid reservoir.

35. The method of claim 34, wherein the step of equilibrating comprises:
    exposing the substance to a semi-permeable material that permits water vapor transfer and prohibits liquid water transfer;
    exposing the liquid in the reservoir to the porous membrane such that the membrane permits vapor transfer and prohibits liquid transfer; and
    allowing the water vapor to reach equilibrium with the reservoir vapor.

36. The method of claim 34, wherein the pores have a maximum diameter in the range of 0.2 to 200 nanometers.

37. The method of claim 33, wherein the transponder is wireless.

38. The method of claim 33, wherein the substance having a water potential to be measured is a plant or tree having xylem conduits for transporting sap water, and the microtensiometer sensor is placed adjacent to a plurality of intact xylem conduits.

39. The method of claim 38, wherein a plurality of microtensiometer sensors are placed at different locations within one plant.

40. The method of claim 38, wherein the step of placing a microtensiometer sensor adjacent to a plurality of intact xylem conduits comprises inserting a plurality of microtensiometer sensors into a plurality of plants, the receiver adapted to receive the output from each transponder coupled to the plurality of microtensiometer sensors.

41. The method of claim 33, wherein the substance having a water potential to be measured is concrete.

42. The method of claim 33, wherein the substance having a water potential to be measured is soil.

* * * * *